United States Patent
Taub et al.

(10) Patent No.: US 9,655,870 B2
(45) Date of Patent: May 23, 2017

(54) HOMEOPATHIC DRUG COMPOSITION AND METHODS OF USE THEREOF

(75) Inventors: Floyd Taub, Silver Spring, MD (US); Neal Koller, Annapolis, MD (US); Char Tara Albert, Timonium, MD (US)

(73) Assignee: FINDCURE.ORG, Aurora, CO (US)

(*) Notice: Subject to any disclaimer, the term of this patent is extended or adjusted under 35 U.S.C. 154(b) by 1008 days.

(21) Appl. No.: 11/701,737

(22) Filed: Feb. 2, 2007

(65) Prior Publication Data

US 2007/0141169 A1 Jun. 21, 2007

Related U.S. Application Data

(62) Division of application No. 10/206,470, filed on Jul. 29, 2002, now abandoned.

(51) Int. Cl.
| | | |
|---|---|---|
| A61K 31/16 | (2006.01) | |
| A61K 31/165 | (2006.01) | |
| A61K 31/27 | (2006.01) | |
| A61K 31/185 | (2006.01) | |
| A61K 41/00 | (2006.01) | |
| A61K 45/06 | (2006.01) | |

(52) U.S. Cl.
CPC ........ *A61K 31/185* (2013.01); *A61K 41/0004* (2013.01); *A61K 45/06* (2013.01)

(58) Field of Classification Search
CPC ..................................................... A61K 31/27
USPC .................................. 514/616, 617, 476, 478
See application file for complete search history.

(56) References Cited

U.S. PATENT DOCUMENTS

| | | |
|---|---|---|
| 4,102,948 A | 7/1978 | Feuer et al. |
| 4,218,404 A | 8/1980 | Feuer et al. |
| 4,629,625 A | 12/1986 | Gaull et al. |
| 4,751,085 A | 6/1988 | Gaull et al. |
| 4,784,992 A | 11/1988 | Reiner et al. |
| 4,929,763 A | 5/1990 | Luetkins et al. |
| 5,370,868 A | 12/1994 | Knight et al. |
| 5,578,313 A | 11/1996 | Knight et al. |
| 5,643,966 A | 7/1997 | Knight et al. |
| 6,007,819 A | 12/1999 | Taub et al. |
| 6,046,241 A | 4/2000 | Knight et al. |
| 6,096,536 A | 8/2000 | Knight et al. |
| 6,166,086 A | 12/2000 | Taub et al. |
| 6,245,561 B1 | 6/2001 | Knight et al. |
| 6,323,025 B1 | 11/2001 | Knight et al. |
| 6,451,853 B1 | 9/2002 | Taub et al. |
| 6,762,174 B1 | 7/2004 | Taub et al. |
| 2001/0008933 A1 | 7/2001 | Taub et al. |
| 2002/0035118 A1 | 3/2002 | Taub et al. |

FOREIGN PATENT DOCUMENTS

| | | |
|---|---|---|
| JP | 49004210 84 | 1/1974 |
| WO | WO 9714306 A1 | 4/1997 |
| WO | WO99/42097 * | 8/1999 |
| WO | WO 99/42099 | 8/1999 |
| WO | WO 9942097 A1 | 8/1999 |
| WO | WO 9942098 A1 | 8/1999 |
| WO | WO 9942116 A1 | 8/1999 |

OTHER PUBLICATIONS

Gennaro et al. Remington's Pharmaceutical Sciences, Seventeenth Edition, 1985, pp. 216-218, 1306-1307.*
Kotz et al. "Chemistry & Chemical Reactivity," Second Edition, 1991, pp. 56-57.

* cited by examiner

*Primary Examiner* — Shengjun Wang
(74) *Attorney, Agent, or Firm* — Nevrivy Patent Law Group P.L.L.C.

(57) ABSTRACT

The present invention comprises homeopathic preparations of compounds, methods for using such preparations and delivery systems for the treatment of disease symptoms through the administration of these homeopathic compositions.

18 Claims, No Drawings

HOMEOPATHIC DRUG COMPOSITION AND METHODS OF USE THEREOF

CROSS-REFERENCE TO RELATED APPLICATIONS

This application is a divisional of and claims priority to U.S. application Ser. No. 10/206,470, filed Jul. 29, 2002 now abandoned, the contents of which are relied on and incorporated herein by reference.

FIELD OF THE INVENTION

This invention relates to homeopathic preparations of compounds as well as methods and systems for delivery of such preparations and treatment of disease symptoms by administering such preparations. In particular, the present invention provides for homeopathic preparations of Taurox compounds.

BACKGROUND OF THE INVENTION

In 1790, while Samuel Hahnemann was translating a materia medica from English into German, he came across a reference that the prevalent prescription for malaria at that time was cinchona bark. The reason stated for its efficacy was that it was quite bitter. Dr. Hahnemann was well versed in the current use of medicine and felt that there must be another reason besides its bitter qualities that made it work because many other medicines were bitter but ineffective in the treatment of malaria. By experimenting on himself, through taking cinchona bark and observing the effects he was able to produce the symptoms of malaria: chills, fever, palpitations, and sweats. These observations were included in his translated text as a footnote.

The more Hahnemann studied and translated medicine and medical texts, the clearer it became to him that if healthy people took massive amounts of a particular drug, the drug would actually cause the same symptoms it was supposed to cure. Hahnemann then reasoned that the symptoms of a sick patient could be matched to symptoms that a drug produced. His experiments along the lines of his reasoning lead to the development of a new branch of medicine, which he called homeopathy, from the Latin words, homeo, meaning the same, and pathos, meaning illness.

In order to demonstrate the effectiveness of a homeopathic drug, the drug is tested by a "proving" in order to see how the drug will effect an otherwise healthy person. Hundreds of compounds have been tested according to such "proving". Homeopathic repertories provide listings of the human anatomy and set forth symptoms that have been observed on such body part and treatments for the symptoms. On the other hand, books referred to as "Materia Medicae" set forth the homeopathic drugs and identify the maladies and symptoms each drug treats. Moreover, where a repertory lists a symptom, it classifies possible treating compounds as either first, second or third degree remedies for that symptom. Typically, a homeopathic practitioner will prescribe first degree indications for a particular symptom although sometimes second indications may be employed on a case-by-case basis. Very seldom would a homeopathic practitioner think to use a third degree indication and such listings are provided only to note that, on rare occasions, that the remedy has been known to cure the symptom but that it is not recognized by a "proving".

The current materia medicas have up to 5,000 proven drugs listed. The drugs are derived from plants, minerals and animal substances. The remedies are listed in alphabetical order in the materia medica. The materia medica has grown to include not just symptoms that were proven but also to include toxicological symptoms as well as symptoms that were actually cured in sick patients using that particular remedy. The symptoms in the materia medica are categorized in order from the top of the body on down. So all the symptoms in the head are categorized together, then the eyes, ears, nose and so on until the extremities.

Some remedies have only 40 symptoms listed in the materia medica, while others have 15,000 symptoms. Since it is impossible to remember all the symptoms of each remedy, about 150 years ago the information was collated into a reference form. All the remedies that affect a certain place in a certain way were placed under a particular category. The book that contained these categories is called a repertory. The categories listed in the repertory are called rubrics.

The repertory of the materia medica is actually a reference tool that lists all the symptoms cured or produced and list every remedy that has treated that particular category/rubric. For example, a rubric might list: Head: pain, above left eye, 3 pm lasting to 6 pm, with one remedy listed under the rubric. Rubrics can be very specific like this one, or very general. A general rubric would be Head; pain, and that general rubric would contain hundreds and hundreds of remedies. The more specific the rubric the better for a homeopath, as it truly indicates a closer match. However, specific rubrics are likely to be too specific and incomplete and therefore misleading.

Hugo Schultz, in 1887, postulated that the effect of a stimulus on a living cell is indirect and proportional to its intensity and quantity. Schultz demonstrated that very low concentrations of yeast toxins increased yeast growth over 100 fold. Around the same time, the psychiatrist Rudolph Arndt developed his "Basic Law of Biology," which states that weak stimuli slightly accelerate the vital activity, middle-strong stimuli raise it, strong stimuli suppresses it, and very strong stimuli halt vital activity. These separate observations were formulated by Arndt in 1888 into one of the earliest laws of pharmacology representing the homeopathic effect, the Arndt-Schultz law, which states: every stimulus on a living cell elicits an activity, which is inversely proportional to the intensity of the stimulus (Martius F. Das Arndt-Schultz Gnindgesetz, Muench Med. Wschr., 1923, 70(31):1005-1006). This law was later restated by Hueppe as: for every substance, small doses stimulate, moderate doses inhibit, large doses kill. Allopathic medicine, with its emphasis on moderate to high drug doses, works to inhibit undesired physical symptoms and to kill undesired pathogens. Homeopathic medicine begins with small doses and moves towards higher and higher dilutions to stimulate the body's own natural defenses.

One of the basic tenets of homeopathic medicine is that a cure for a disease can be evoked by using a high dilution medicine that resembles but is different from the cause of the disease. Homeopathy is widely accepted as a useful therapeutic throughout Europe, the British Commonwealth countries and India, and has been demonstrated to have characteristic and reproducible effects. A critical review of more than 100 controlled and/or clinical studies of homeopathy determined that patients received positive healing benefits from homeopathy beyond the placebo effect (Kleijnen, J. et al. 1991 Brit. Med. J. 302:316-323; Linde, K., Clausius, N., Ramirez, G., Melchart, D., Eitel, F., Hedges, L. V., Jonas, W. B., 1997, Lancet, 350:834-843; Reilly, D., et al, 1994, Lancet, 344:1601-1608).

After a base preparation is made, either by an extract or maceration of an herbal compound or the dissolving of a selected compound in a solvent, a series of dilutions are prepared from the initial batch, called the "mother tincture". Homeopathic drugs are diluted according to either the decimal "X" or centesimal "C" scales. For a "3X" preparation, the mother tincture is diluted with nine parts of the desired diluent, in either liquid or powder form. The resultant mixture is then diluted a second time, in a ratio of one part mixture to ten parts solvent and the resulting mixture is diluted a third time in a ration of one to ten. Therefore, the 3X drug is actually at $10^{-3}$ potency of the mother tincture. Similarly, a 6X dilution would be at $10^{-6}$ potency of the original solution. In the "C scale" each dilution is done with ninety-nine parts diluent to the original mixture. Therefore, a 3C solution is at $10^{-6}$ potency of the original mixture and thus corresponds to a 6X potency. These scales are recognized by the Homeopathic Pharmacopeia of the United States (H.P.U.S.).

Many homeopathic medicines are used at concentrations of micrograms ($10^{-6}$ M) and nanograms ($10^{-12}$ M); however, in other homeopathic preparations, the dilutions exceed Avogadro's number ($6.023 \times 10^{-23}$). When compounds are diluted 1:10 (or 1:100), with repeated succusions (violent shaking or pounding) and repetitively diluted by this procedure these compounds are prepared and labeled as homeopathic remedies. A variety of dilution or attenuation methods are known in the art, the most common methods are the Hannemannina and the Korsakovian methods. If a dilution has been repeated at least 24 times, a potency is achieved ($10^{-24}$) that is so highly dilute that the statistical probability of a single molecule of the original substance remaining in the volume used is low. Homeopathic practitioners believe that the original molecules effect a change in the solvent and that each successive dilution further increases both this change and the potency of the remedy regardless of the presence of molecules of the original material in much the same manner as bronze casting reproduces an original sculpture made of wax or clay with the need for wax or clay in the final sculpture. In traditional homeopathic practice, a frequent homeopathic dosage is 10-15 drops of a $10^{-12}$ molar, or 6 C, solution administered two to three times per day. A $10^{-60}$ molar or 30 C may be given one to three times per day. A $10^{-400}$ molar or 200 C may be given only one time per month or year. The beneficial activity of such highly diluted remedies are derived exclusively from the changes in the energy field or the solvent of the remedy caused by the original molecules. Scientific researchers at Harvard University have reported that changes in NMR spectra of the solvent occur as a result of this process.

In contrast many homeopathic medicines, especially combination products and those sold OTC, have dilutions between 2x and 24x. Especially those at dilutions between 3x and 10x have very substantial number of molecules and thus their beneficial effects are a summation of the physical chemical effects of the molecules plus the energy and enhanced solvent effects. This invention applies equally to these low dilutions and to the super molecular dilutions described above. For general use the preparations with significant number of molecules remaining 2x to 20x are a preferred embodiment of this invention.

A scientific discipline called "hormesis" has recently received increasing acceptance. This field documents that low doses of otherwise toxic materials are not toxic and may produce ill defined but clearly beneficial effects. This phenomenon has not previously been used therapeutically. One aspect of this invention is that doses labeled hormetic are not only not toxic but may be used in a therapeutic manner. The dose range that this phenomenon occurs is below that of standard pharmaceutical or toxicological effects. It is often but not necessarily above the dose used in homeopathic medicine. The scientific principle behind it is akin to the principle of homeopathy. Although these preparations may not be prepared by the classical methods of homeopathic pharmacists they are included in the definition of homeopathic preparations for the purpose of this invention.

Analogous to chemical homeopathy/hormesis it has been found that, contrary to the accepted views on radiation, that low doses of radiation (including that given off by radon) are not harmful. One aspect of this invention is that low doses of radiation defined herein as a homeopathic dose of radiation is prophylactic and therapeutic.

Highly dilute homeopathic medicines have been effective in treating some conditions, including viral infections, in vivo. For example, homeopathic dilutions of $1 \times 10^{-200}$ to $1 \times 10^{-1000}$ of typhoidinum, hydrophobinum, tuberculinum, nux vomica and malandrinum caused 100% inhibition of pock-like lesions caused by a chicken embryo DNA virus on the chorio-allantoic membrane as compared to controls (Singh, L. M. and Gupta, G. 1985 Brit. Homeopathy 74:168-174). In contrast, the same medicines at different homeopathic concentrations, or control phosphate buffered solution (PBS), had lesser or no effect.

A common principle of homeopathy is the Law of Similars, which was founded in the science of pharmacology and states that a drug has two effects on the body, a direct effect and the subsequent reaction of the body to the drug, evoking symptoms or side effects. This approach follows a rule that, where a substance produces a specified disease symptom or indication at a high dosage level in a healthy person, that symptom will be effectively treated in an ill person by a substantially dilute dose of the same substance. In other words, a symptom of a disease may be treated by a minor amount of a compound that will cause such symptom in a healthy person when administered at greater levels. The U.S. FDA defines homeopathy as "the practice of treating the syndromes and conditions which constitute disease with remedies that have produced similar syndromes and conditions in healthy subjects." The U.S. FDA accepts as a homeopathic drug "any drug labeled as being homeopathic which is listed in the *Homeopathic Pharmacopeia of the United States* (HPUS), an addendum to it or its supplements. The potencies of homeopathic drugs are specified in terms of dilution, i.e., 1×⅒ dilution, 2×⅟₁₀₀ dilution, etc. Homeopathic drug products must contain diluents commonly used in homeopathic pharmaceutics. Homeopathic drugs are for the most part, natural substances, although synthetic substances can be used. They are distributed as over the counter, through mass distribution channels without physician prescription, or as prescription, through highly controlled channels requiring physician prescription. The operative principals for homeopathic drugs are to utilize very low concentrations of drug, generally well below the Minimum Toxic Dose (MTD) for humans, and to manufacture them in a certain way with certain materials generally by a series of dilution steps with a defined process of vigorous agitation, termed succussion, between each step. Homeopathic drugs, due to their low concentrations. Homeopathic OTC drugs, in particular, are considered very safe and thus distributed through mass market channels. Homeopathic OTCs are ubiquitous and readily available to the general populace via the same or similar channels as vitamins, foods and nutritional supplements. Other drugs, sometimes known as standard drugs, allopathic drugs or ethical pharmaceuticals, are natural or synthetic substances usually presented for use at high concentrations much nearer the potentially toxic level. Allopathic drugs thought to be safe for the general population may also be categorized as over the counter and may be distributed through mass distribution channels without physician prescription. Allopathic drugs, when available by prescription, are distributed through highly controlled channels requiring physician prescription. Allopathic drugs are manufactured under strict methods and utilize materials that are specific to each drug. Thus, the distribution of allopathic drugs is very controlled and they are not readily available to the general populace.

The U.S. FDA specifies a dietary supplement product may make no statements on the effect it has on the structure or function of the body as distinguished from drug claims that a product diagnoses, treats, prevents, cures, or mitigates disease. Dietary supplements should be presented at concentrations very far away from their toxic doses; they are distributed through mass market channels, are ubiquitous and readily available to the general populace, similar to vitamins and foods.

Table 1 is a comparison of the toxic doses for various classes of ingestible compounds and shows the relationship of the above compounds with their toxic doses.

| TOXIC DOSE COMPARISON | |
| --- | --- |
| Ingestible Compound | Toxic Dose Level |
| Ethical Pharmaceutical | 0.1–0.5 toxic dose level |
| OTC Drug | 0.1–0.3 toxic dose level |
| Dietary Supplement | 0.001–01 toxic dose level |
| Homeopathic Medicine | <0.000001 toxic does level |

Because homeopathic drugs are at very low concentration levels, far from their toxic dose they are very safe. This safety reduces the need to establish a detailed, extensive body of scientific evidence that presents their disease performance characteristics. As a result there is considerably less detailed information for homeopathic drugs versus other drugs. Additionally, contributing to the limited scientific evidence for homeopathic drugs, is the fact that homeopathy has been known and used for hundreds of years reducing the need and arguing against the expense to perform detailed modern scientific and clinical trials. Another reason for reduced scientific information for homeopathic drugs is the process to present a homeopathic drug to the user follows a shorter and less costly regulatory approval process versus allopathic drugs. As a consequence, the performance characteristics and benefits of homeopathic drugs are not nearly as well known to the caregiver and patient communities as are other drugs. In fact, one fundamental tenant of homeopathy is that each patient is an individual. The ideal remedy for one patient is thus likely to be counterproductive for another. Homeopathic physicians use their skill in evaluating individual patients to choose appropriate remedies. As the remedies are not toxic initial use may be considered a therapeutic trial and the physician will adjust the remedy and dose dependent on the clinical results seen in that patient. Population statistics are of no or limited value to homeopathic physicians or individual patients. Homeopaths believe that most patients are not approximated by an average or median, i.e. size M does not fit all.

Allopathic drugs, as a result of their high concentrations near toxic levels, are required to have extensive scientific evidence of safety and efficacy before they are presented for use. The cost and time to develop allopathic drug's scientific evidence to satisfy the regulatory approval process are much greater than the cost and time for homeopathic drugs.

Because Dietary Supplements are so very far away from their MTD and because they make no disease claims, the need to establish a detailed, extensive body of scientific evidence that presents their performance is nonexistent. While they fall under regulatory control, the regulatory requirements in dietary supplements are limited mainly to the primary compliance with truth in advertising requirements only. This approval process requires statistical documentation of statistical likelihood of success before a drug may be sold. Nevertheless therapy is individualized for each person and successful therapy of most all chronic diseases requires numerous drug and dosage adjustments for that patient. Genomics is the current term allopathic medicine is using to justify unique treatment of individuals, a position analogous to that traditionally used by homeopaths.

There is a great need for drugs that are very safe as a result of low concentrations, which are given at concentrations far from their toxic level and that frequently result in benefits to the patients. These drugs are defined by scientific evidence of characteristics and benefits based on disease performance similar to allopathic drugs and are readily available through mass distribution channels similar to foods or nutritional supplements. Such low concentration/high potency/scientific evidence based/mass distribution channel drugs are more effective because their scientific evidence of performance and benefits is based on disease experience and claims which allow users to make better decisions and achieve healthier life status.

SUMMARY OF THE INVENTION

Accordingly, the homeopathic preparations of the present invention are non-toxic and do not produce undesirable side effects. They can be formulated and provided to a large patient population at a reasonable cost by means of delivery systems that are convenient and safe. Homeopathic preparations of the present invention are preferably administered via oral or topical delivery systems, or using eye drops, nasal or throat sprays, transdermal delivery, or other routes of administration except for those designated to be given by prescription they do not involve injection and that do not require sterile equipment or the participation of health care professionals. Alternatively, the present invention may also be administered by means of intracutaneous, intramuscular, intravenous, or subcutaneous injection or given under the care of a health practitioner.

The homeopathic preparations of the present invention preferably comprise one or more potencies of 3,3'-(dithiodi-2,1-ethanediylamino)bis[-N-(3-oxopropyl carbamic acid)] or carbobenzoxy alanyl taurine (herein after "Taurox SB") at a concentration, or homeopathic potency, of less than about $10^{-6}$ molar, and more preferably between about $10^{-6}$ molar and about $10^{-100,000}$ molar. Some of the homeopathic preparations may thus contain few or no molecules of Taurox SB however a more preferred embodiment will contain significant numbers of molecules. Homeopathic preparations of the present invention are defined as comprising Taurox SB if the preparation is derived from or originated from a preparation comprising a measurable quantity Taurox SB.

Additional features and advantages of this invention will be set forth in the description that follows, and will in part be apparent from the description or may be learned by practice of the invention. The objectives and other advantages of the invention will be realized and obtained by the process particularly pointed out in the written description and the claims hereof.

To achieve these and other advantages and in accordance with the purpose of the invention to provide a homeopathic preparation of Taurox SB. It is also an object of present invention that the homeopathic preparation of Taurox SB include additional components such as vitamins, minerals, amino acids and other traditional homeopathics.

It is an object of the present invention to provide a homeopathic composition comprising Taurox SB having a homeopathic potency selected from the group of dilutions consisting of 2X, 3X, 4X, 5X, 6X, 7X, 8X, 9X, 10X, 11X, 12X, and so on to 24X H.P.U.S. It is a further object of the present invention to administer the homeopathic composition in a liquid form, particularly as an aerosol spray.

It is an object of the present invention to provide a new and useful homeopathic composition that is effective in treating or ameliorating symptoms arising from degenerative changes or infectious diseases or proliferative diseases or metabolic disease disorders. These symptoms may arise as a result of viral infections, immune reactions, immune disorders and fatigue.

It is a further object of the present invention to provide a new and useful homeopathic composition that can be used to treat and/or ameliorate the symptoms of a particular individual whose physiology would benefit for this remedy. In homeopathy it is know that the appropriate remedy for a person will adjust his or her body so that an illness, regardless of the allopathic proximate cause, will be treated or ameliorated.

Another object of the present invention is to provide a homeopathic composition which can be administered orally in the treatment viral infection, particularly rhinovirus, influenza virus, hepatitis B virus, hepatitis C virus, herpes virus (CMV, HSC and EBV) and HIV infections.

It is a further object of the present invention to provide a homeopathic composition which can be administered orally in the treatment of bacterial, fungal, parasitic and prion infections. A further object of the present invention provides a homeopathic composition which can be administered orally in combination with other remedies.

Still a further object of the present invention is to provide a homeopathic composition at selected potencies that effectively treats the symptoms arising from degenerative changes, physiological disorders, metabolic disorders, proliferative disorders, immune dysfunctions, infectious processes, viral infections, immune reactions, immune disorders and fatigue.

According to the present invention, a homeopathic composition is disclosed for use in treating symptoms arising from outbreaks of bacterial infections, proliferation abnormalities, degenerative changes, viral infections, immune reactions and fatigue. This homeopathic composition comprises a mixture that includes Taurox SB. Preferably, this mixture includes a dilution of Taurox SB in a potency range of 3X to 24X.

In any event, this mixture may include a pharmaceutically acceptable carrier solvent, preferably ethanol, and the mixture may be processed into a dosage unit selected from a group consisting of tablets, capsules, pellets (globules), liposomal sprays, wafers, lactose pillules and gel caps. Alternatively, the mixture includes a pharmaceutically acceptable topical preparation, preferably selected from a group consisting of ointments, creams, lotions, liquids, liposomal ointments and gels. A further object of the present invention includes a pharmaceutical topical preparation that is a hydrophilic ointment.

The present invention also contemplates administering the composition in a dosage unit is in a dry form wherein the solution includes a ethanol carrier solvent and wherein the solution is placed in a selected quantity of a pharmaceutically acceptable dried compound and processed to allow a majority of the ethanol and other carrier solvent(s) to evaporate. Moreover, the dosage unit may be administered orally from one to three to four times per day until relief is achieved. The oral administration may include the step of placing the composition under the tongue of the patient. The present invention also contemplates administering the composition as a cream or ointment by applying the homeopathic composition topically to the immune response eruption one to three to four times per day.

The present invention also contemplates intermittent or single day use. It is an object of the present invention to provide a method for modulating additive cravings or compulsive behavior. In particular, the present invention provides a method to modulate cravings for tobacco, marijuana, and other drugs of addiction, food cravings, other addictions and other compulsive behaviors. The present invention contemplates in modulating additive cravings or compulsive behaviors by administering the composition multiple times per hour.

It is a further object of the present invention to provide a method for modulating virus levels in the serum of a patient comprising administering an effective amount of the homeopathic composition a patient. In particular, the present invention provides for a method for modulating the virus levels or decreasing the symptoms of Hepatitis B virus, Hepatitis C virus, CMV, HSV, EBV and HIV. It is an object of the present invention to provide a method for modulating fatigue in a patient by administering an effective amount of the homeopathic composition to such a patient.

It is an object of the present invention to provide a method for modulating immune reactions and immune dysfunctions, particularly insufficient immune response and allergic reactions in a patient by administering an effective amount of the homeopathic composition to a patient in need of treatment. It is an object of the present invention to provide a homeopathic composition that is a liposomal preparation. In particular, the liposomal preparation is selected from a group consisting of ointments, creams, lotions, liquids and gels.

It is an object of the present invention to provide a homeopathic composition made by either the Hannemannian or Korssakovian methods of attenuation (dilution).

DETAILED DESCRIPTION OF THE INVENTION

The present invention is directed to homeopathic preparations. Several compounds have been developed which fall within the definitions of a drug. Some of these definitions are located in articles recognized in the official United States Pharmacopeia, official Homeopathic Pharmacopeia of the United States, or official National Formulary, or any supplement to any of them or their equivalents abroad. These drugs are extremely potent but may be used at concentrations significantly below minimum toxic dose. These drugs when prepared by the classic homeopathic procedures are most appropriately tested and prescribed or used by the methods for classical homeopathic products. These preparations are safe for mass marketing through, for example, dietary supplement marketing channels.

Compounds of the present invention include beta-alethine (U.S. Pat. No. 6,245,561, incorporated by reference in its entirety herein), beta-alanyl-taurine, carbobenzoxy beta-alanyl-taurine (U.S. Pat. No. 6,096,536, incorporated by reference in its entirety herein) and other modifications of beta-alethine or beta-alanyl-taurine. In a preferred embodiment, the compound 3,3'-(dithiodi-2,1-ethanediylamino)bis[N-(3-oxopropyl carbamic acid)] or carbobenzoxy alanyl taurine is manufactured in a specific, dilution step method using known diluents, each step completed by a vigorous shaking process termed succussion. Taurox SB is a low molecular weight benzyl sulfonic acid and is also known as Immuvant and TaurImmune. Taurox SB is a chemical modified form of a chemical combination of the nutrient taurine and a derivative of the amino acid alanine. Taurine is a "conditionally essential" nutrient in the development and support of brain and retina tissue and an important component of human breast milk and formulae's. Alanine is a non essential amino acid. The structural formula of Taurox SB is shown below:

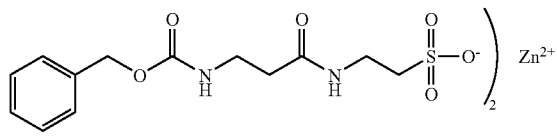 [SMILES: O=C(CCNC(=O)OCc1ccccc1)NCCS(=O)(=O)[O-] ; [Zn+2]]

Taurox SB may generally be supplied at three different concentrations in 20.0% ethanol/80.0% water designated respectively: Rx, OTC, and Ped strengths. However once of ordinary skill in the art would know that Taurox SB may be supplied in any concentration in a variety of mixtures and designated in any manner. Taurox SB is preferably stored at ambient temperature (generally 20° to 25° C.; 68° to 77° F.) but may also be stored in a broader temperature range.

Taurox SB has been evaluated in homeopathic provings included in its Materia Medica are increasing energy, effective against headaches, colds, viruses, allergies, muscle aches and pains, PMS as well neurological problems, appetite abnormalities, irritable bowel syndrome or loose stools and coughs. One of the target patient populations to receive the homeopathic composition of the present invention are those patients with historically documented, measurable symptoms relevant to the Materia Medica and/or pharmacology of Taurox SB. Taurox SB may be administered to patients to treat, ameliorate or prevent any of the following symptoms: Sub-optimal immune function as indicated by chronic or recurrent disease states, viruses, colds, flu, hepatitis, HIV, human papilloma virus infections (warts) infecting the laryngeal, skin, and genitals, coughs, bronchitis, bronchiectasis, COPD, recurrent urinary track infections, recurrent upper respiratory infections, seborrheic keratosis, lichen planus, dysplasias, basal cell carcinomas as well as other cancers, periodontal disease, and immune deficiency diseases. Another target population is those patients suffering from immune conditions such as allergy, irritable bowel syndrome and loose stools, asthma, fibromyalgia and psoriasis. Similarly, those patients with metabolic conditions such as cachexia (cancer or viral related), fatigue ("chronic fatigue" or viral, immune, or cancer-related fatigue) and appetite abnormalities are also included as a target population of patents to receive the homeopathic composition of the present invention. Also included in the target population of patients to receive the homeopathic composition are those patients who suffer from pain and/or central nervous system ailments such as headaches, muscle aches and pains, premenstrual syndrome (PMS) and neurological problems. A further target population of patients to receive the homeopathic compositions are patients with addictions to tobacco, marijuana, alcohol, and other drugs of abuse such as cocaine, heroin, amphetamines and morphine. Still another target population of patients to receive the homeopathic compositions are patients with compulsive behaviors that are addictives (possibly due to endogenous release drug-drug like molecules).

The homeopathic preparations of the present invention typically comprise between $1\times10^{-6}$ and $1\times10^{-100,000}$ molar concentrations or between 2x and 10x of Taurox SB in a pharmaceutically acceptable diluent. Homeopathic preparations preferably comprise a concentration of 2X or less and alternatively or additionally, $1\times10^{-6}$ M Taurox SB or less and, alternatively or additionally, comprise a concentration of $1\times10^{-12}$ M Taurox SB or less, preferably a concentration of $1\times10^{-24}$ M Taurox SB or less, and in some cases comprise a concentration of $1\times10^{-60}$ M Taurox SB or less. Homeopathic preparations of the present invention preferably comprise a homeopathic potency of Taurox SB of one or more of the following potencies: 2X or more to 20X or 1C or more to 220C or 1M or more to 100M. Homeopathic preparations are prepared under standard scales of attenuation and preparation under which each successive attenuation (or dilution) or trituration contains just $\frac{1}{10}$, $\frac{1}{100}$, or $\frac{1}{50,000}$ as much drug substance as the preceding attenuation. These scales are know as the decimal (X), the centesimal (C) and the fifty millesimal systems (ML) (HPUS Abstracts, 2001, incorporated by reference in its entirety herein). Under the decimal scale of attenuation, one gram of tincture, one milliliter of 1X solution or gram (1.0 g) of 1X trituration represents 0.1 gram of a dry crude medical substance. One milliliter of 2X attenuation, or 1 gram of second trituration contains 0.01 gram of the dry crude medicinal substance. Subsequent attenuations are made by serial progression, succussing or triturating one part of the preceding attenuation to nine parts of the vehicle. Thus a 3X liquid contains $10^{-3}$ gram of the dry crude medicinal substance. Under the centesimal scale of attenuation, one milliliter of the first centesimal liquid attenuation (1 C) or one gram of the first centesimal trituration represents 0.01 gram (10.0 mg) of the dry crude medicinal substance. Subsequent attenuations are made by serial progression, succussing or triturating one part of the preceding attenuation to ninety-nine parts of the vehicle. Thus a 3C attenuation has $10^{-6}$ gram of the dry crude medicinal substance. Under the fifty millesimal scale of attenuation, one milliliter of the first millesimal attenuation (1 LM) represents $4.0\times10^9$ g of dry crude medicinal substance. One milliliter of the second millesimal attenuation (2 LM) represents $8.0\times10^{14}$ g of dry crude medicinal substance.

Homeopathic liquid attenuations are designated according to the method of attenuation. The designations, which must appear on the labels are X or D on the decimal scale made by the Hahnemannian method of attenuation, CH or C on the centesimal scale made by the Hahnemannian method of attenuation, CK or K on the centesimal scale made by the Korsakovian method of attenuation, LM on the fifty millesimal scale made by the Hahnemannian method of attenuation. A Korsakovian attenuation uses a clean stoppered glass vial of appropriate capacity into which a measured volume of the substance is added. The vial is succussed followed emptying of the vial to remove 99 percent if the original volume. To the remaining 1 percent original volume 99 part diluent is added to make the first Korsakovian attenuation (1 CK). The process is repeated resulting in a 2 CK dilution or attenuation.

While these are the classic methods of dilution or attenuation one skilled in the art may readily make virtually equivalent preparations using alternative methods of dilution and/or succussion and alternative volumes and weights of materials. Such alternative methods are included within this invention. Note that uppercase and lower case (x, c, ml) are used interchangeably Homeopathic Preparations of Taurox SB 1X Taurox SB A homeopathic preparation of 1X Taurox SB starts with 1.0 g of TAUROX SB weighed into a clean 10 ml volumetric flask fitted with ground glass stopper followed by the addition of USP purified water to just below the mark. Using Karl Fisher titration, add proportionately more than 1.0 g based on the water content of sample. The flask is stopped and shaken to dissolve the TAUROX SB. If any undissolved solid remains, the preparation is solicited and warmed until the solid is dissolved. After cooling to room temperature, USP purified water is added to the mark and mixed well. This solution contains 1.0 g of solids in 10.0 ml of solution that is the correct ratio for a 1× Solution (Class A, HPUS).

2X Taurox SB

A 2X homeopathic TAUROX SB composition is prepared by first transferring the contents of the prepared 1X composition contained in the 10 ml volumetric flask to a tarred 125 ml Erlenmeyer flask with a ground glass stopper. The transfer is effected using about 40-60 ml of USP purified water followed by the drop wise addition of water to 100.0 g. This preparation will have 1.0 g of solids in 100.0 ml of solution that is the correct ratio for a 2× Solution. The flask is stopped and succussed.

3X Taurox SB

A 3X homeopathic TAUROX SB composition is prepared by weighing 5.0 g of the 2X concentrate into a tarred 125 ml Erlenmeyer flask labeled 3X with a ground glass stopper. Purified USP water is added to 50.0 g, the flask is stopped and successed. As another option, any other weight of 2X may be used so long as the final weight of this step is 10 times the weight of 2X homeopathic TAUROX SB used and the container size is adjusted to be not less than 40% or more than 75% full. (The best amount to work with is 67% of the capacity of the container).

4X Taurox SB

A 4X homeopathic TAUROX SB compositions is prepared as above for the 3X Taurox SB except the 3X preparation is used as the starting material. Once succussed the resulting product is 4X homeopathic TAUROX SB.

5X through 10X Taurox SB

The 5X through 10X compositions are prepared using a 20% solution in enough volume to make the desired final product volume. Briefly, each preparation is made by adding to a clean 100 ml graduated cylinder 21 parts of alcohol, USP (95% ethyl alcohol), followed by adding purified USP water to 100 mls volume. The resulting 20% (v/v) alcohol solution is transferred to a clean container and mixed well. Optionally, the alcohol and water may be weighed into a container such that the final composition is 20% Alcohol, USP by volume. The density of Alcohol, USP (95% ethyl alcohol) is about 0.82 g/ml and water is 1.00 g/ml. Using a tarred clean dry 10 ml volumetric flask the weight is determined the weight and hence the density of a 10.0 ml sample of the 20% alcohol solution.

A 5X homeopathic TAUROX SB composition is prepared by weighing 10.0 g of the 4X homeopathic TAUROX SB composition into at tarred 250 ml Erlenmeyer flask with ground glass stopper, followed by the addition of a sufficient weight of the 20% alcohol solution to make 90.0 mL. For example: if the density of the 20% alcohol solution is 0.96 g/ml then to make 90 mls of solution 86.4 g of solution is needed to make 180 ml. The flask is stopped and succussed.

A 6X homeopathic TAUROX SB composition is prepared using the density value for the 20% alcohol solution to calculate the weight of 140 ml of 5X homeopathic TAUROX SB composition required (e.g. if the density is 0.96 g/ml weight would be 134.4 g of 5X). That weight is measured into a 2,000 ml Erlenmeyer flask with ground glass stopper and diluted to 1,400 ml with 20% alcohol solution. Calculate the weight needed for this dilution (i.e. the weight needed to add 1,260 ml) in the same way as for 5X homeopathic TAUROX SB. Stopper and succuss. This produces 6× homeopathic TAUROX SB.

A 7X homeopathic TAUROX SB composition is prepared using the steps as described for the 6X homeopathic TAUROX SB, and using a tarred 250 ml Erlenmeyer flask with a ground glass stopper. The amount of 6X homeopathic TAUROX SB equivalent to 14 ml of solution (about 13.4 g) is weight and 20% alcohol solution is added to 140 ml. The flask is stopped and succussed.

A 8X homeopathic TAUROX SB composition is prepare by transferring all 140 ml of 7X homeopathic TAUROX SB composition to a tarred 2,000 ml Erlenmeyer flask with ground glass stopper. Again the volume of solution required is calculated using the density and sufficient a weight of 20% alcohol solution is added to make the volume ten times that of the 7X. The flask is stopped and succussed.

A 9X homeopathic TAUROX SB composition is prepared by transferring 13 g (14 ml) of 8× homeopathic TAUROX SB to a tarred 250 ml Erlenmeyer flask with ground glass stopper and adding a sufficient weight of 20% alcohol solution to make the volume ten times that of the starting volume of 8×(total about 140 ml or 134.4 g). The flask is stopped and succussed.

A 10X homeopathic TAUROX SB composition is prepared by transferring all 140 ml of the 9X homeopathic TAUROX SB to a tarred 2,000 ml Erlenmeyer flask with ground glass stopper. The volume of solution is calculated before, using the density and a sufficient weight of 20% alcohol solution is added to make the volume ten times that of the 9× homeopathic TAUROX SB. The flask is stopped and succussed.

General Manufacture:

Other volumes than described above may be used. All dilutions should conform to the 1/10 v/v ratios described in the above or others to meet traditional homeopathic guidelines. However this invention is not limited to strict adherence to the exact recipes as described herein as there are numerous ways of generating virtually equivalent preparations which are known those skill in the art.

The typical guidelines for preparation of the preferred embodiment follow. No container should be too full to success effectively (for example not less than 40% full and not more than 75% full). Ideally the volume to success is about 67% of the capacity of the container. The original concentrate (1X or 2X) should not be stored and used to make further solutions (unless they are maintained sterile) as they must be freshly prepared due to the absence of alcohol. For 3X and later concentrations the preceding dilution can be used. For example, additional 4X can be made from stored 3X. It is suggested to make any dilution in 20% alcohol if it is to be stored for later use. Homeopathic TAUROX SB made in 20% alcohol can be stored at room temperature. Therefore, if a 3× stock homeopathic TAUROX SB is desired it should be prepared from the freshly made 2X homeopathic TAUROX SB using 20% alcohol as the diluent. Subsequent dilutions from the stored 3X homeopathic TAUROX SB must be prepared with 20% alcohol. All materials used to prepare homeopathic TAUROX SB dilutions must be clean and reserved only for the manufacture of homeopathic TAUROX SB.

Various diluents or substrates may be used, depending on the desired delivery system. Appropriate diluents for the following delivery systems are well known: oral administration in liquid or solid form; eye drops; nasal sprays; throat sprays; injectables; topical preparations; and transdermal preparations. One or more potencies of Taurox SB and/or one or more additional constituents, such as a purified growth factor, vitamins, minerals, amino acids, or traditional homeopathic preparations, may be combined in a preparation. The preferred homeopathic diluents for oral administration are a solution of purified water, glycerin, citric acid and a preservative such as sodium benzoate; or a solution of purified water, glycerin, potassium sorbate, and/or a form of proteinated-copper in a cationic state, and a preservative such as sodium benzoate. Other diluents for oral delivery, including various alcohol-containing solutions, are known in the art and may be employed in the present invention to increase solubility and stability of Taurox SB. The homeopathic preparations of the present invention are preferably administered orally, but may also be prepared in topical formulations for application to the skin; administered transdermally; by intracutaneous, intramuscular, intravenous, or subcutaneous injection; or administered in the form of eye drops or nasal and throat sprays. Lotions for topical and transdermal application, and buffered salt solutions for eye applications, are well characterized and widely used in the cosmetic industry, which are readily adaptable to the preparation of the present invention. Additionally, carrier solutions for intranasal administration of substances are well known in the art and widely used in drug delivery systems.

In a preferred embodiment, homeopathic preparations of Taurox SB are prepared in a tablet form that dissolves in the mouth. The tablets are made from a suitable organic material, such as lactose (Dolisos, Las Vegas, Nev.), or sucrose by methods well known in homeopathy, as described in the United States Homeopathic Pharmacopoeia. In particular, tablets are generally produced in two forms, as tablet triturates or compressed tablets. Tablet triturates are produced by preparing a homeopathic preparation of Taurox SB, and adding binders as necessary. Binding solutions are composed of a binder, such as gum arabic, microcrystalline cellulose, a preservative if necessary, an inert lubricant, and purified water. The tablets are then molded by hand or preferably by automated equipment, and the tablets are then dried by introducing them into a dehumidified environment with a relative humidity of 3540%, and an ambient temperature of 70 to 110° F. Compressed tablets are formed by compression of a dry material and contain no special coating. They are compressed from powdered or crystalline solids, and, as with tablet triturates, may contain binders, excipients, lubricants, and disintegrators. Compressed tablets are produced by adding the homeopathic preparation of Taurox SB to the lactose preparation until thoroughly moistened. Binders may be added at this time as necessary, as described above for tablet triturates. The moistened material is granulated by passing through an appropriate mesh screen, and the moistened granulation is introduced into a dehumidified environment and subsequently dried as described above. The dried granulation is then regranulated through the mesh screen and lubricants, such as mineral oil, talc, calcium stearate, corn starch, are added as necessary. The mixture is then compressed in a rotary tablet compressor or any similar apparatus to the desired tablet size.

One preferred embodiment is inclusion in a single liquid, pellet or other form two or more potencies for example a 6X and a 20C might be included in a single preparation. This may result in a preparation advantageous for several reasons including obtaining full benefit of molecular and submolecular functionalities.

Taurox SB Pre-Clinical Studies

Pharmacology Studies—Human Cells in Culture

Taurox SB was shown to enhance components of early T cell activation, including increased intracellular calcium, up regulated expression of the CD69 T cell activation marker and enhanced proliferation of peripheral mononuclear cells in culture (Dunn et al, 2000, incorporated by reference in its entirety herein). Tumor necrosis factor alpha (TNF-alpha) and interferon gamma message were also up regulated in the presence of Taurox SB, unless the cells also were exposed to high levels of exogenous stimulation in which case a normalization was seen. Taurox SB decreased or did not change the amount of secreted TNF-alphamessage (which might cause toxicity) while causing enhanced expression of active cell surface protein. Taurox SB increased granzyme activity in T cells. The Taurox SB—mediated increase in surface TNF-alpha, was able to effect killing of HL60 tumor cells in vitro. While some effects require high does, serial diluted and vigorously agitated low doses alter bioelectric properties and the key cell signal mobilization.

Whole Animal Laboratory Studies

The result of the chemical synthetic process beginning with beta-alethine specified in Knight, et al (incorporated by reference in its entirety herein) 1994 results in a molecule now identified as Taurox SB. (Knight et al, called the molecule made by this process the benzyl derivative of "Vitalethine"). In vivo studies where Taurox SB was the sole agent, it was shown to have potent anti-tumor effects against melanoma and myeloma models at low doses with negligible toxicity. (Knight et al 1994, incorporated by reference in its entirety herein).

Taurox SB may also be effective at stimulating immune response following a single injection of antigen. Taurox SB may help avoid the problems of local irritation and necrosis and the systemic symptoms found with complete Freund's adjuvant (CFA). The choice of CFA as the gold standard for antibody production in the pn14-protein conjugate system is supported by the data from van de Wijgert et al, 1991 regarding alternative adjuvants (Immunogenicity of streptococcus pneumoniae type 14 capsular polysaccharide. *Infection and Immunity*, 59(8):2750-7, incorporated by reference in its entirety herein). No adjuvant gave a greater total IgG response than CFA, and CFA caused an approximately 10-fold greater IgG response to pn14-BSA conjugate than no adjuvant.

In a preferred embodiment of the present invention, homeopathic Taurox SB increases the effectiveness of a vaccine or otherwise modifies an immune response.

Toxicology Studies:

Several studies suggest that TAUROX SB (as other attenuated substances) has an unusually wide margin of safety between the effective dose and the amount of material that can be harmful. Single-dose studies of TAUROX SB in adult male and female CD-1mice suggested a maximally tolerated dose (MTD) of about 150 mg/kg administered as an IV bolus. Acute toxicology studies performed by MidAtlantic Bio-Research did not demonstrate an acute lethal response until doses exceeding 133 mg/kg of TAUROX SB were reached. From a study performed by Dovetail Technologies, Inc. no toxic side effects were observed following either oral or subcutaneous daily doses of 400 ug/kg of TAUROX SB for 9 days. During the 14-day post-administration period, the animals all gained the appropriate amount of weight as compared to their saline-injected controls and there was no morbidity/mortality. Following euthanasia there were no abnormal findings in the gross necropsies. Similar findings were obtained in animals receiving 2000 mg/kg orally for 14 days. Thus, the toxic doses levels of the compounds appear high (assuming a similar biochemical pathway and not correcting for a different surface-area-to-weight ratio), a dose of 9,975 mg (9.9 g) would not be lethal for a 75-kg person.

Human Studies

Safety: As of Mar. 30, 2001, a total of 39 normal volunteers have received from 14 to 28 doses of TAUROX SB as part of the homeopathic proving process, without any severe adverse effects. As of Jul. 18, 2002, over 40 patients with various complaints have participated in clinical trials for 1-6 months (1-2 drops of 8× or 6× daily), without any severe adverse effects. Many of those patients report improvements in their conditions (see below)

Efficacy:

Thirty-nine (39) patients have completed the first homeopathic proving trial. The study design was a true double blind and placebo-controlled. An apparent physiological placebo effect was observed in 26% of patients where placebo was given. In contrast, 92% of those receiving TAUROX SB were identified as having physiologic affects by the evaluating physician who did not know whether the subjects were receiving placebo or drug. While there is too little data from the clinical trials on most medical conditions to assess efficacy, benefits for some indications are suggested by the preliminary data (see below).

This double-blind placebo-controlled "proving" study was performed by David Riley. (Riley, Proving Report—Taurox SB. David Riley, M.D., Integrative Medicine Institute, Apr. 16, 2001, incorporated by reference in its entirety herein).

Rationale

TAUROX SB pre-clinical data suggest that Taurox SB may play a role in immune stimulation. TAUROX SB studies of human cells in culture suggest a calcium dependent mechanism leads to increased proinflammatory cytokine production in unstimulated cells and an immune modulation in highly stimulated cells. TAUROX SB animal toxicity studies suggest that the proposed dose is over 1 million-fold lower than the toxic dose. TAUROX SB initial human experiences in the homeopathic proving process are consistent with low toxicity and immunomodulation. Numerous potential applications were suggested.

The symptoms and liver degeneration in patients with hepatitis are caused by an interaction of the virus and the person's own immune system. Immune system molecules (cytokines) are known to cause fatigue. Immune system molecules and immune system cells cause allergies.

The allopathic pharmaceutical activity of Taurox SB is described in Dunn et al, *Immunostimmulatory Effects of Taurox SB™*, U MD, Dept. of Cell Biology and Molecular Genetics, manuscript submitted for publication; Dunn *Immunostimmulatory Effects of Taurox SB™*, Thesis, Univ. of MD, Dept. of Pharmacology and Experimental Therapeutics, 2000, incorporated by reference in its entirety herein. In contrast, homeopathic Taurox SB has been diluted, potentized and prepared according to accepted homeopathic practices. One drop per day is taken under the tongue. This dosage is far below the lowest dose found to have any allopathic pharmaceutical effects in the above studies. Although the drop contains many billions of molecules (about 1,000,000,000,000 molecules) but still has less than one millionth the dose of standard pharmaceutical drugs.

EXAMPLE 1

Decreased Fatigue Studies

Table 2 shows the clinical data of the eight patients who entered the study with at least moderate fatigue (24 pts or higher). They all experienced reduced fatigue while taking Taurox SB.

TABLE 2

Decreased Fatigue
(Lower numbers indicate less fatigue)

| Patient ID | Week of Study | | | | | | | | | | | | | | | | | | | | | | |
|---|---|---|---|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| 101 | 28 | 27 | 24 | 24 | 27 | 26 | 20 | 16 | 16 | 20 | 14 | 14 | 19 | 19 | 20 | | 21 | 19 | 19 | 17 | 15 | 16 | 16 |
| 102 | 41 | 48 | 47 | 48 | 40 | 35 | 48 | 48 | 48 | 46 | 37 | 35 | 22 | 22 | 22 | | | | | | | | |
| 103 | 37 | 31 | | 24 | | 21.5 | | 9 | | | | | | | | | | | | | | | |
| 201 | 29 | 39 | 36 | 21 | 23 | | | | | | | | | | | | | | | | | | |
| 202 | 30 | 39 | 25 | | | 17 | 10* | | | | | | | | | | | | | | | | |
| 401 | 25 | 20 | 29 | 21 | 9 | 8 | | | | | | | | | | | | | | | | | |
| 507 | 33 | 32.5 | 31 | | | | | | | | | | | | | | | | | | | | |
| 703 | 48 | 44 | 44 | 44 | 44 | 41 | | 37 | 41 | 41 | 32.5 | 39.5 | 39.5 | 39.5 | 39.5 | | | | | | | | |

To date, many patients have experienced reduced fatigue and improved sleep after taking Taurox. For example, Patients 103, a 49-year-old male, entered the study with Chronic Fatigue Syndrome, allergies, oral herpes and fibromyalgia. He took the 8× dose for about 2 months. He reported increased energy, no eruptions of herpes and one cold that resolved more quickly than usual. He noted some decrease in frequency of allergy and fibromyalgia symptoms.

Patient 202 has breast cancer and melanoma and entered the study for fatigue and PMS. She reported, greater energy and better sleep. Patient 507 has arthritis and Irritable Bowel Syndrome (IBS). She reported less fatigue and improvement in IBS. Patient 703 has severe Chronic Fatigue Syndrome and numerous other conditions, including IBS. She reports less fatigue and complete resolution of IBS. Additional patients who had fatigue and allergies are described in the allergies example below.

Summary: All eight patients with at least moderate fatigue report improvements. The average score decreased by 43% This change is statistically significant (p=0.002).

EXAMPLE 2

Decreased Allergies

Table 3. Table 3 is the clinical data from all patients who reported at least moderate allergies at the pre-study. Most patients reported a decrease in allergies while taking Taurox SB.

TABLE 3

Allergy Study
(Lower numbers indicates less frequent allergies)

| Patient ID | Week of Study | | | | | | | | | | | |
|---|---|---|---|---|---|---|---|---|---|---|---|---|
| | 0 | 1 | 2 | 3 | 4 | 5 | 6 | 7 | 8 | 9 | 10 | 11 |
| 102 | 10 | 10 | 10 | 10 | 10 | | | 8.5 | 8.5 | 8.5 | 8.5 | 10 | 10 |
| 103 | 8 | 7 | 3 | | 3 | | 3 | | 3 | 3 | | |
| 402 | 6 | 3 | 2 | 2 | 3 | | | | | | | |
| 201 | 10 | 5 | 1 | 0 | 1 | | | | | | | |
| 701 | 10 | | 10 | 10 | 10 | 10 | 10 | | | | | |
| 401 | 9 | 9 | | 3 | | 3 | 2 | 2 | | 3 | 4 | 3 |
| 702 | 10 | 10 | 10 | 5 | 6 | 3 | | | | | | |
| 703 | 10 | 10 | 10 | 10 | 10 | 10 | 10 | 10 | 10 | | | |

Patient 102, a middle-aged female, entered the study with lymphocytopenia, allergies, cough, PMS, fibromyalgia and muscle aches and pains. On the 8X dose, her lymphocyte count improved and she reported improvements in energy, an overall feeling of well-being and less pain.

Patient 702, a middle-aged female, entered the study with massive uterine fibroids, allergies, fatigue and PMS. On the 8X dose, she reported marked reduction of her severe allergic response to known allergens, such as perfume, less severe PMS, less discomfort from the fibroids and improved ability to work.

Patient 401 has lung cancer; she entered the study because of fatigue and allergies. On the 8X dose for 3 months, her allergy symptoms were less frequent and less severe. She believes the drug is helping with her recovery from chemotherapy. She has been able to maintain her appetite and weight and has less fatigue.

Summary: Five of the eight patients with significant allergies report a 82% average reduction in symptom frequency. This change is statistically significant (p=0.017).

EXAMPLE 3

Decreased Hepatitis C Viral Load

Table 4 indicates the hepatitis C viral load in a patient.

TABLE 4

| Hepatitis C Viral Load | |
|---|---|
| Nov. 23, 2001 | 2.59 |
| Jan. 7, 2002 | 1.84 |
| Jan. 25, 2002 | 1.49 |
| Feb. 13, 2002 | 1.89 |

TABLE 4-continued

| Hepatitis C Viral Load | |
|---|---|
| Feb. 26, 2002 | 0.99 |
| Mar. 26, 2002 | 1.92 |

Patient 101 is a middle-aged Asian female, who is thought to have contracted Hepatitis C (genotype 1) through a blood transfusion in 1984. In mid 1992, she was notified of the viral antibodies in her system through a rejected blood donation, though she did not become symptomatic until late 1992. In 1999, she had received Interferon Alpha Therapy (IFN). After an initial good response, she failed IFN therapy due to viral escape. IFN caused severe deliberating side effects, severe fatigue, weight loss, low White Blood Cell counts and depression. It provided only temporary stoppage of viral proliferation. The patient entered the Taurox SB study in late 2001 due to fatigue. She took Taurox SB at strengths of 6X or 8X over a period of 4 months. Her viral load decreased by about 40% on average and her overall mood also improved. Test results showed that patient 101 had a maximal viral load decrease of 62%.

Patient 101 also reported less fatigue on both doses. The largest decrease in viral count and fatigue occurred on 6X Taurox SB. The previously required daily naps became unnecessary upon initiation of 6X Taurox SB. After she completed the trial and stopped taking Taurox SB, she frequently required lengthy daily naps. Her liver enzymes decreased on Taurox SB as compared to both pre- and post-Taurox treatment.

Recently, a second HCV patient began therapy. This patient (number 706) has also experienced decreased fatigue on Taurox SB. Quantitative HCV counts are not available on this patient.

What is claimed is:

1. A method for treating or preventing fatigue in a subject in need thereof, which comprises administering to the subject an effective amount of a homeopathic composition,
   wherein the homeopathic composition is prepared by (a) dissolving carbobenzoxy alanyl taurine, or a salt thereof, into a solvent to achieve a first solution and (b) serially diluting and succussing the first solution using the solvent to achieve the desired homeopathic potency; and
   wherein the fatigue is not caused by cancer and infection.

2. The method of claim 1, wherein the effective amount ranges between 1 to 20 drops of the homeopathic composition per dose.

3. The method of claim 1, wherein the homeopathic composition has a homeopathic potency selected from the group consisting of 5X, 6X, 7X, 8X, and 9X.

4. The method of claim 3, wherein the homeopathic potency is 6X or 8X.

5. The method of claim 1, wherein the homeopathic composition further comprises at least one component selected from the group consisting of: a vitamin, a mineral, an amino acid, a fatty acid, a plant extract, and another homeopathic remedy.

6. The method of claim 5, wherein the component is a traditional homeopathic composition.

7. The method of claim 1, wherein the homeopathic composition is administered via a route selected form the group consisting of an aerosol spray, sublingually, orally, transmucosally, and injection.

8. The method of claim 1, wherein the homeopathic composition is impregnated on a solid medium.

9. The method of claim 8, wherein the solid medium is selected from the group consisting of tablets, capsules, pellets, globules, and gel caps.

10. The method of claim 8, wherein the solid medium comprises an oral quick dissolve composition.

11. The method of claim 1, wherein the solvent is ethanol, glycerol, water, or a combination thereof.

12. A method for treating or preventing fatigue in a subject in need thereof, which comprises administering to the subject an effective amount of a homeopathic composition,
wherein the homeopathic composition: (a) has a homeopathic potency selected from the group consisting of 5X, 6X, 7X, 8X, and 9X; and (b) is prepared by (i) dissolving carbobenzoxy alanyl taurine, or a derivative or salt thereof, into a solvent to achieve a first solution and (ii) serially diluting and succussing the first solution using the solvent to achieve said homeopathic potency; and
wherein the fatigue is not caused by cancer and infection.

13. The method of claim 12, wherein the effective amount ranges between 1 to 20 drops of the homeopathic composition per dose.

14. The method of claim 12, wherein the homeopathic composition has a homeopathic potency selected form the group consisting of 6X and 8X.

15. A method for treating or preventing fatigue, which comprises providing a patient with an effective amount of a homeopathic composition, wherein the homeopathic composition (a) comprises carbobenzoxy alanyl taurine, or a salt or derivative thereof, and (b) is prepared using the Hahnemannian or Korsakovian method of attenuation or dilution.

16. The method of claim 15, wherein the effective amount ranges between 1 and 20 drops of the homeopathic composition per dose.

17. The method of claim 15, wherein the homeopathic composition has homeopathic potency selected from the group consisting of 5X, 6X, 7X, 8X and 9X.

18. The method of claim 17, wherein the homeopathic composition further comprises at least one component selected from the group consisting of: a vitamin, a mineral, an amino acid, a fatty acid, a plant extract, and another homeopathic remedy.

* * * * *